United States Patent
Stegmüller et al.

[11] Patent Number: 6,096,082
[45] Date of Patent: Aug. 1, 2000

[54] MODULAR INSTRUMENT SYSTEM FOR KNEE JOINT PROSTHESES

[75] Inventors: Nicolas Stegmüller, Bienne; Sven Wanner, Winterthur; Richard Buni, Hettlingen, all of Switzerland

[73] Assignee: Sulzer Orthopaedie AG, Baar, Switzerland

[21] Appl. No.: 09/198,812

[22] Filed: Nov. 24, 1998

[30] Foreign Application Priority Data

Nov. 28, 1997 [EP] European Pat. Off. .............. 97810927

[51] Int. Cl.⁷ ...................................................... A61F 2/38
[52] U.S. Cl. .............................. 623/20; 606/102; 606/89
[58] Field of Search .............................. 623/20; 606/86, 606/88, 89, 90, 100, 102

[56] References Cited

U.S. PATENT DOCUMENTS

| | | |
|---|---|---|
| 4,474,177 | 10/1984 | Whiteside . |
| 4,944,760 | 7/1990 | Kenna . |
| 5,037,423 | 8/1991 | Kenna ........................................ 606/86 |
| 5,431,656 | 7/1995 | Clift . |
| 5,611,802 | 3/1997 | Samuelson ................................ 606/86 |
| 5,649,928 | 7/1997 | Grundei ..................................... 606/89 |
| 5,728,128 | 3/1998 | Crickenberger .......................... 606/102 |
| 5,735,904 | 4/1998 | Pappas ....................................... 623/20 |
| 5,792,143 | 8/1998 | Samuelson ............................... 606/102 |

Primary Examiner—Michael J. Milano
Attorney, Agent, or Firm—Townsend and Townsend and Crew LLP

[57] ABSTRACT

With the invention a modular instrument system for knee joint prostheses is shown. A shaft (1), which can be provisorily but rotationally fixedly anchored along the anatomical axis (4) of the distal femur bone (2), terminates in the direction towards the joint with a collar (6). A parallel guide (7) is provided in the direction of a mechanical axis (9) from the collar (6) towards the interior of the shaft (1), which stands off by a guide angle a towards the medial to the shaft axis, which coincides with the anatomical axis (4). A coupling piece (10) with a projecting guide part (8) which is displaceably journalled in the parallel guide (7) serves as a reception for manipulation condyles (23) in order to test and determine the ideal position with respect to a tibia platform in the end positions of the articulation before resection blocks are positioned with the fixed coupling piece (10) for the final resection. The collar (6) is particularly advantageous in re-operations as a reference abutment (30).

10 Claims, 4 Drawing Sheets

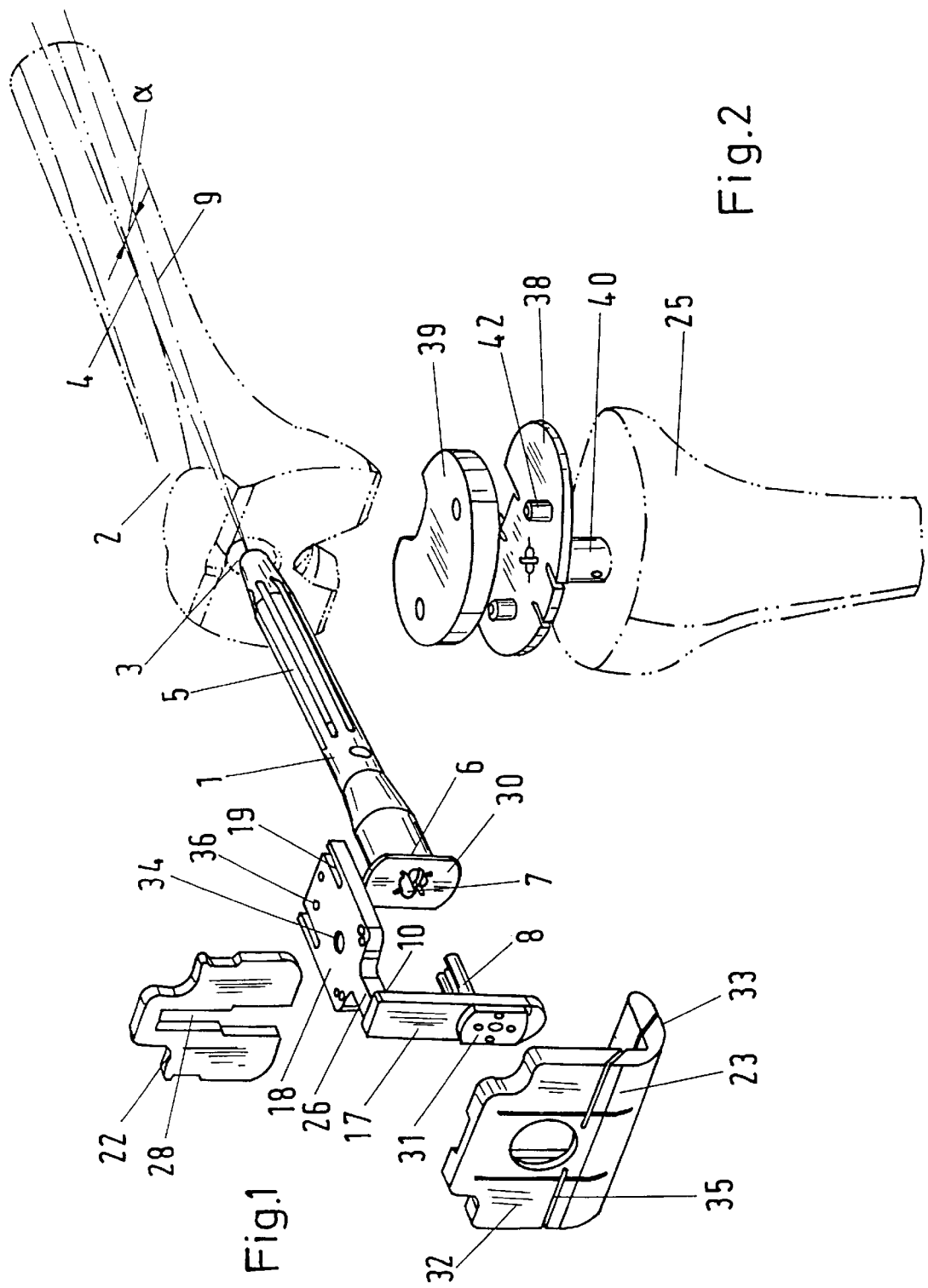

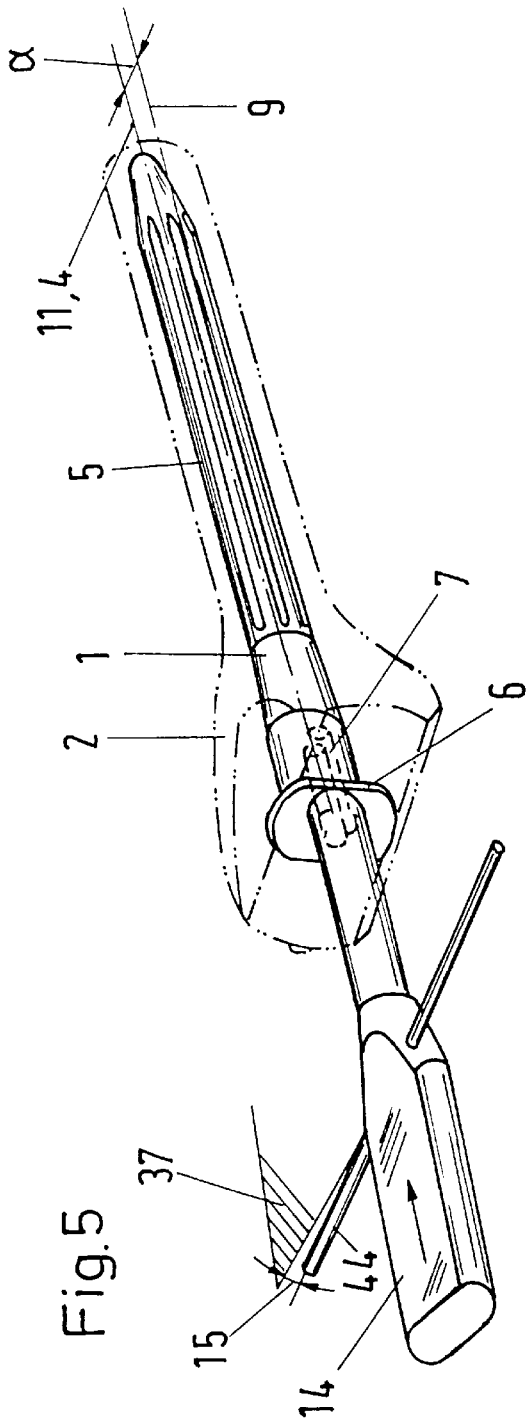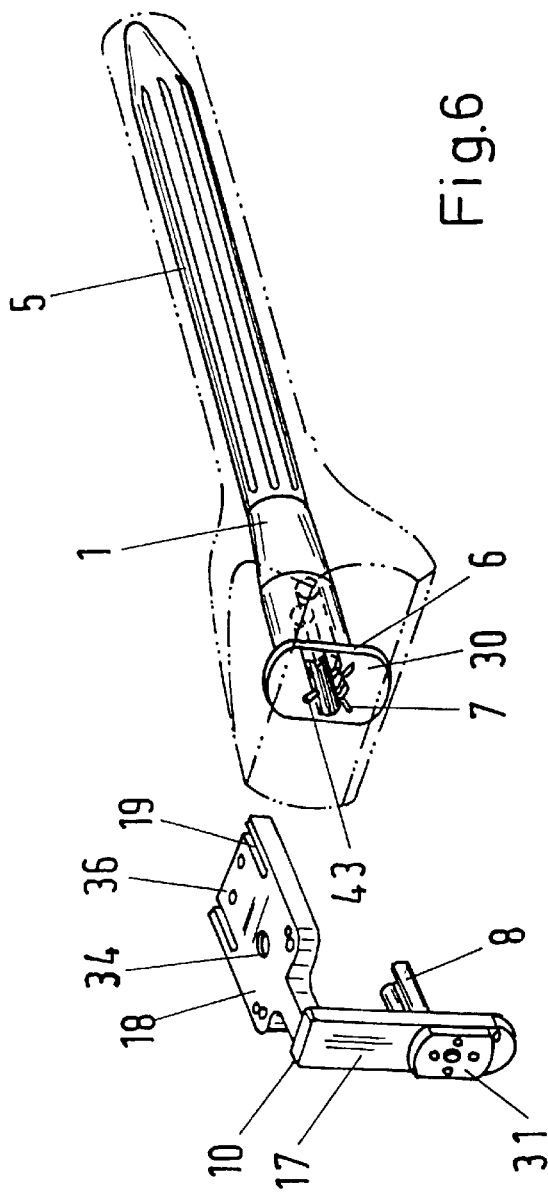

MODULAR INSTRUMENT SYSTEM FOR KNEE JOINT PROSTHESES

BACKGROUND OF THE INVENTION

The invention relates to a modular instrument system for knee joint prostheses with a provisorially anchorable shaft which is provided at the distal end of a femur bone for the insertion into a bore in the direction of the anatomical axis.

A modular instrument system for knee joint prostheses is shown in U.S. Pat. No. 4,759,350 which uses a bore which is placed into the marrow cavity in the direction of the anatomical axis as an orientation aid for an instrument arrangement in which the position of the mechanical axis is determined by the transversal contact plane of the femur condyle which is perpendicular to it. For this a bar is placed into the bore along the anatomical axis at the projecting stump of which an auxiliary plate is pivotal to such an extent that it lies in contact with both femur condyles in order to fasten them afterwards with nails at the femur condyles in an angled off position for a first resection at the anterior side of the femur condyles. Then a second auxiliary plate is placed onto the just cut resection surface and oriented by means of insertable bolts to the first auxiliary plate and fixed onto this resection surface with nails in order to make a resection at the front end. The previously cut resection surfaces are in each case used as reference surfaces for the further gauges and resection blocks and abutments. An instrument set of this kind presupposes an extremely precise operating by the orthopedist, since tools are continually being changed and oriented to previously cut resection surfaces. The situation becomes even more difficult when parts of the condyles are already missing—whether due to their destruction or whether it is a matter of a re-operation—in order to determine the orientation of the mechanical axis required as an initial position.

SUMMARY OF THE INVENTION

The object of the invention is to eliminate these disadvantages. It satisfies the object in that the shaft has projections for the rotationally fixed anchoring, in that the shaft has a terminating collar as a reference abutment for instruments and in that the shaft has an inwardly lying parallel guide for a projecting guide part of a coupling piece, with the parallel guide being rotationally fixedly arranged in the direction of a mechanical axis which is pivoted towards the medial direction by a guide angle a with respect to the shaft axis, which coincides with the anatomical axis.

The invention has the advantage that a shaft, which can be predetermined with respect to its measurements and with respect to the parallel guide at a suitable guide angle a by virtue of the X-ray photographs of the femur and the tibia, can be fastened provisorially in the femur bone at a suitable displacement angle and serves as a reference for all further operations at the femur. In particular the final resection at the end face can be done after the determination of the suitable artificial femur condyles and after the testing of their functioning with test condyles in the two end positions of the articulation.

Although the shaft can be practically completely sunk in the femur and thus nowhere stands in the way of later manipulations, its angle of rotation with respect to a frontal or sagittal plane can be checked during the driving in by means of a positioning reception for the driving-in apparatus and an angle display can be placed thereupon.

The coupling piece is then executed at the guide part as an angled piece with two limbs which are successively bent off at 90° and which serve without obstruction as reference surfaces for further instruments. In order to take up the torques produced by these instruments, the shaft has projections in the form of longitudinal ribs. In addition longitudinal slits are provided on the second limb, which extends parallel to the guide part and through which guide pins can be driven in into the femur in order to take up even greater torques via the longer lever arm between the parallel guide and the longitudinal slits. The collar of the shaft serves as a reference abutment for spacers which can be pushed in between the manipulation condyles and the collar in order to determine the ideal position of the later condyles through a controlled articulation. Since the collar of the shaft forms an independent reference in the mechanical axis, this arrangement proves useful in particular in re-operations in which the collar no longer lies in contact with the femur bone because an associated resection had already been made previously. The definitive position of the guide part with respect to the parallel guide in the longitudinal direction can be fixed at the femur with nails through bores of the second limb in order to make all further resections for the artificial condyles from the same basis. Since the suitable size of the articulation can be tested with manipulation condyles at a manipulation platform of the tibia before definitive resections are made, the reliability is increased for the surgeon. At the same time the operating time becomes rather shorter with a universal coupling piece which can be displaced in the direction of the mechanical axis. Angles are provided for the guide angle a which correspond for example to a valgus angle of 3°, 5° or 7°. The number of shafts required is reduced if they are executed in two pieces with a connector in order to combine different shaft lengths with different guide angles a. Decisive in this for the setting tool for the driving in is that the setting tool can be placed on at a definite angular position with respect to the arrangement of the parallel guide.

The invention will be explained in the following with reference to exemplary embodiments.

BRIEF DESCRIPTION OF THE DRAWINGS

FIG. 1 is an exploded view of a shaft with a coupling piece for a femur and a manipulation condyle which can be fastened at the coupling piece with a spacer which can be pushed on determining the distance between the manipulation condyle and the shaft;

FIG. 2 is an exploded view of a manipulation platform of a tibia prosthesis which goes with FIG. 1;

FIG. 5 shows a driving-in apparatus with a shaft driven in in the femur;

FIG. 6 shows the driven-in shaft of FIG. 5 and a coupling piece which is ready for insertion.

DESCRIPTION OF THE PREFERRED EMBODIMENTS

Figure 3:
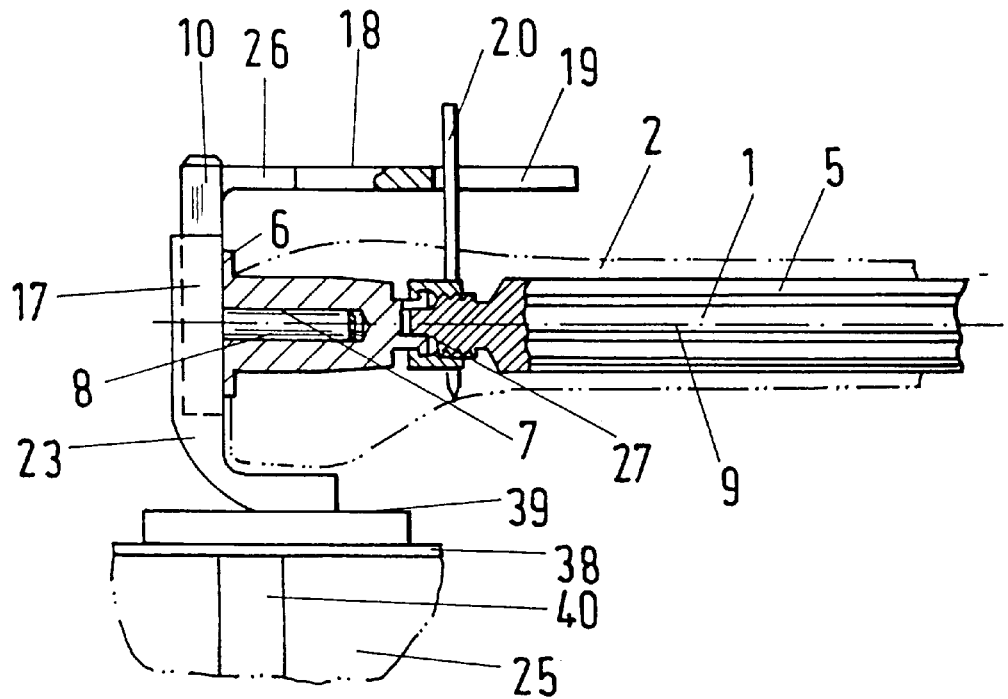
FIG. 3 is a side view of the manipulation condyles of FIG. 1 and FIG. 2 in an angled position.

A modular instrument system for knee joint prostheses is shown in the figures. A shaft 1, which can be provisorially but rotationally fixedly anchored along the anatomical axis 4 of the distal femur bone 2, is terminated in the direction towards the joint by a collar 6. From the collar 6 towards the interior of the shaft 1 a parallel guide 7 in the direction of a mechanical axis 9 is provided which stands off towards the medial by a guide angle a from the shaft axis, which coincides with the anatomical axis 4. A coupling piece 10 with a projecting guide part 8, which is displaceably journalled in the parallel guide 7, serves as a reception for manipulation condyles 23 in order to test and determine the ideal position with respect to a tibia platform in the end positions of the articulation before resection blocks are positioned with the fixed coupling piece 10 for final resections. The collar 6 is particularly advantageous in re-operations as a reference abutment 30.

FIG. 1 shows a femur bone 2 with a bore 3 in the direction of its marrow chamber with an anatomical axis 4, the angle a of which with respect to the mechanical axis 9 of the femur can already be predetermined in the planning of the operation, e.g. by means of X-ray photographs. A shaft 1 which fits the bore 3 and has an inwardly directed parallel guide 7, which stands off from the shaft axis 11 towards the median by an angle a, is driven in by a drive-in apparatus 14 and anchors itself in the femur in a rotationally fixed manner with projections 5 in the form of longitudinal ribs (see FIG. 5). A coupling piece 10 has a projecting guide part 8 consisting of two pins which are connected by a transverse web and can slide back and forth in the parallel guide 7. The parallel guide 7 consists of two bores which are connected to form an elongate hole, with fractions of a middle bore with threaded parts having remained in place in this connection piece in order to be able to receive securing screws. The shaft, which can be sunk in the femur, terminates with a collar 6 of which the end face serves as an abutment 30 and as a reference along the mechanical axis for various instruments.

It is clear that shafts with differing angles a, with differing diameters and with differing lengths are available in order to cover a certain spectrum of cases.

The coupling piece 10 contains a first limb 17 at right angles to the guide part 8 with a mounting 31 for further instruments. A second limb 18, which projects proximally over the femur 2 at a distance parallel to the guide part 8, serves as an auxiliary guide with guide slits 19 and has mountings in the form of threaded holes 34 and bores 36 for further instruments. The second limb 18 opens in a narrow yoke 26 into the first limb 17 in order to be able to insert spacers 22 over the yoke 26 between the first limb 17 and the abutment 30, with the spacers 22 being guided via a slit 28 at the yoke 26.

A manipulation condyle 23, which in this case also has guide slits 35 for possible saw incisions, can be mounted at the front surface of the first limb 17, with the limb 17 dipping into the condyle 23 to such an extent that both are flush in the direction towards abutment 30 and a distance to the abutment 30 which is determined with the condyle 23 and a given spacer 22 is also reproducible without the condyle. The manipulation condyle 23 has a front surface 32 and a posterior surface 33 which correspond to the position of the actual artificial condyles.

FIG. 2 shows a manipulation platform 38 which can be anchored in the tibia 25 with a pin 40. Bearings of different heights with bearing surfaces 39 can be pushed onto pins 42 of the manipulation platform 38.

Figure 4:
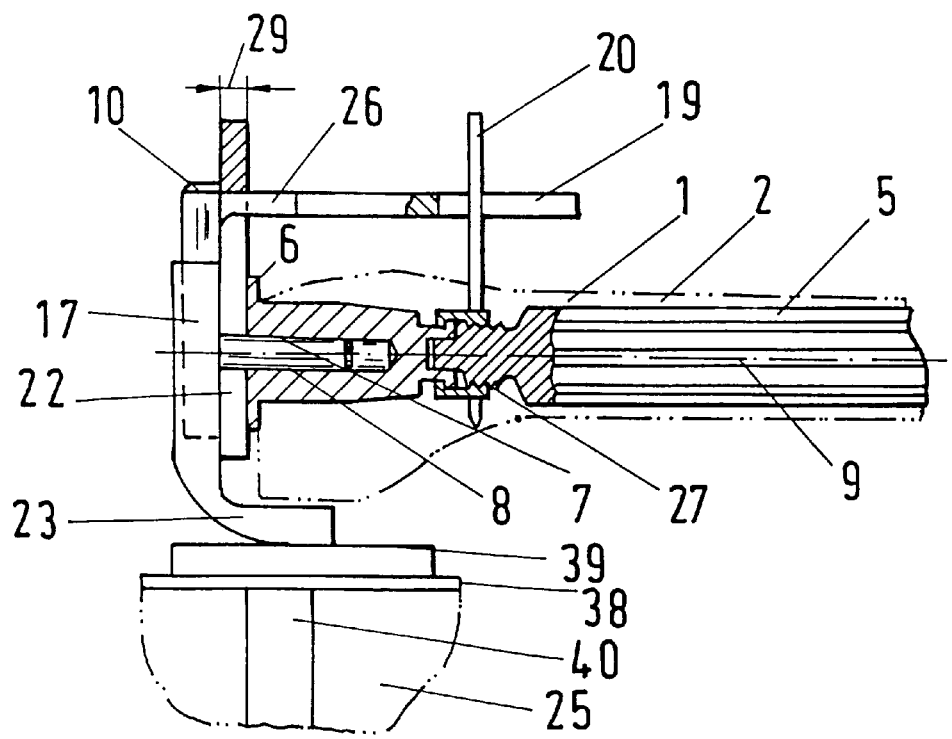
FIG. 4 shows an arrangement in accordance with FIG. 3 in which however the femur-side manipulation condyle is displaced in the direction of the mechanical axis by the thickness of the spacer.

FIGS. 3 and 4 show the cooperation of the manipulation condyles 23 with the manipulation platform 38. In FIG. 3 the shaft 1 is driven into the femur bone 2 and provisorily anchored against rotation with its ribs 5. The shaft itself is built up of two pieces. An anchoring pin of suitable length is rigidly connected via a lock 27 to the part of the parallel guide 7. The pushed on coupling piece 10 with the limb 17 and the manipulation condyles 23 lies in flush contact with the collar 6. With the help of non-illustrated lateral ligaments, the position of the femur 2 and the tibia 25 and the ligament tension can be checked at the two end positions of the articulation and varied at the femur side through the insertion of spacers 22 of different thickness 29 (see FIG. 4) and at the tibia side through different bearing heights until an ideal length has been found. For the reliable guide of the coupling piece 10 support elements 20 in the form of nails are driven in through the guide slits 19 in the femur bone 2 and give additional lateral support. When the ideal position of the coupling piece 10 in the direction of the mechanical axis 9, which coincides with the shaft axis in the side view, has been determined, the second limb 18 is fixed with further nails through bores 36. The manipulation condyles 23 and the spacers 22 can be removed in order to make resections with resection blocks which are suited to the spacer and the condyle size.

Figure 7:
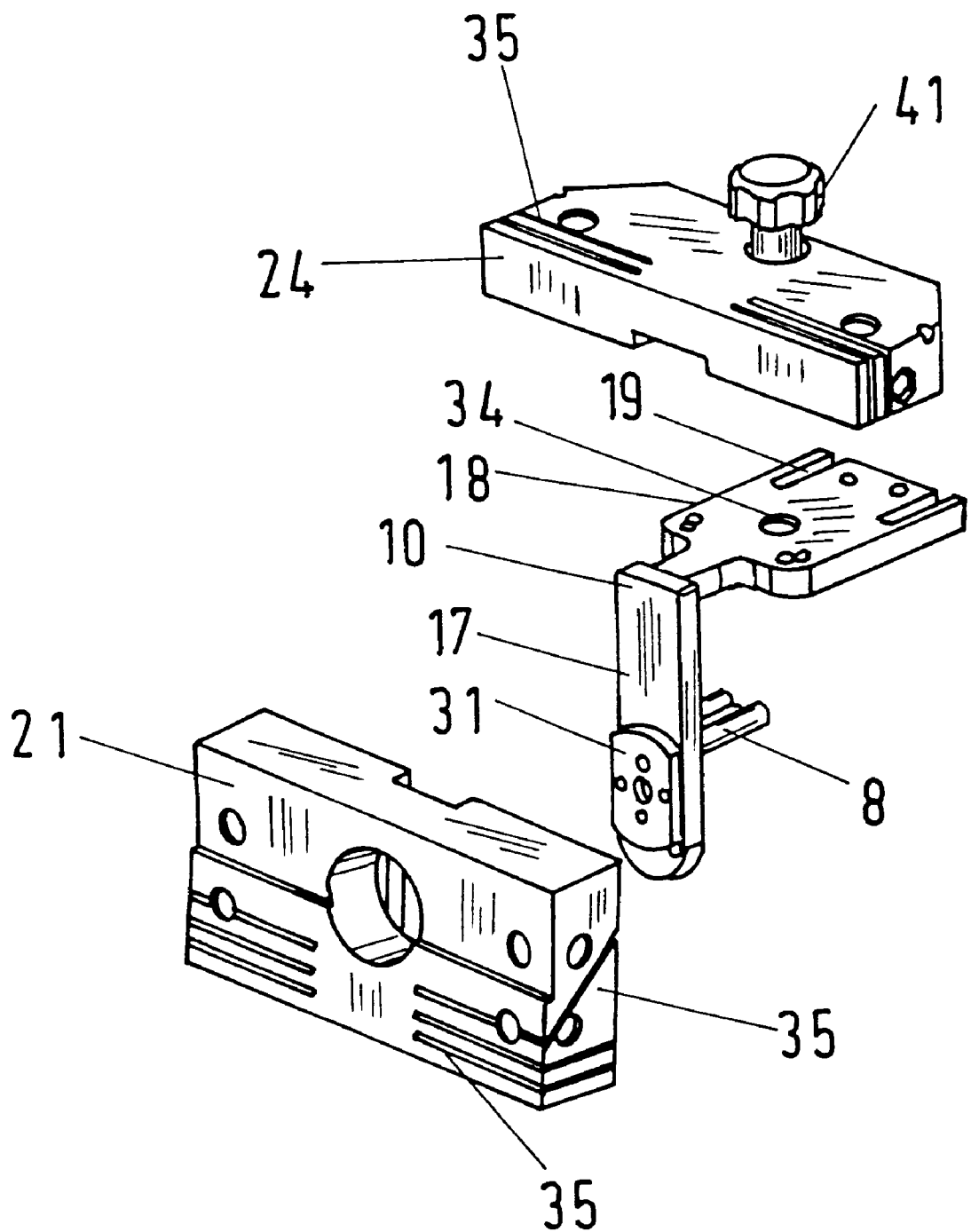
FIG. 7 shows a coupling piece in accordance with FIG. 1 and FIG. 6 with resection blocks which can be fastened to it.

In FIG. 7 a frontal resection block 21 which is provided with guide slits 35 can be secured to the first limb 17 with the mounting 31 analogously to the manipulation condyle. A further resection block 24 can be secured to the second limb 18 with a securing screw 41 in the aligned position in order to cut with an insertable saw blade a final frontal resection surface which corresponds to the gradation of the artificial condyles and their associated spacers.

The driving in of the shaft 1 and the change to the coupling piece 10 will be described with reference to FIGS. 5 and 6. A bore lying along the anatomical axis 4 has already been prepared. The femur bone 2 has resection surfaces from an earlier prosthesis, which can however no longer be used. The femur itself lies with its anatomical axis in a frontal plane 37. The drive-in device 14 is coupled to the shaft via vanes (not shown) which engage in slits 43 at the collar 6 in such a manner that the shaft axis 11 and the axis of the parallel guide 7 lie in a same plane and an angle display 44 in the form of a projecting bar lies in a parallel plane. During the driving in, the shaft axis 11 centers itself automatically along the anatomical axis 4. The surgeon need only observe that the angle display 44 remains parallel to the frontal plane 37 in order that an angle of rotation 15 is held as well as possible at 0°. In this way the parallel guide 7 is applied with sufficient precision along the mechanical axis 9 of the femur bone 2 since the guide angle a between the shaft axis 11 and the parallel guide 7 was chosen in accordance with the previously determined angle between the anatomical axis 4 and the mechanical axis 9 of the femur. Another possibility of improving the accuracy during the driving in consists in driving in a pin at the height of the epicondyles in each case—that is, laterally in the center—and using these pins to find out the angle of rotation zero. The driving in itself can be done with a hammer or an electrically driven striking head. The shaft is driven in to a pre-planned depth in the femur, with the depth being at least so great that the abutment surface 30 of the collar 6 can be used for the instruments to come later. The coupling piece 10, which can be pushed on, is associated with the limb 17 perpendicularly to and with the limb 17 parallel to the guide part 8. Abutment edges and mountings 31, 34, 36, 19 are arranged on both limbs for the instruments to come later.

The principle of the provisorially fixed shaft with a collar as reference can in principle also be used in re-operations on the tibia side, with however the parallel guide being provided along the shaft axis since the mechanical axis and the shaft axis practically coincide in the tibia.

What is claimed is:

1. Modular instrument system for knee joint prostheses comprising a provisorially anchorable shaft (1) which is provided at the distal end of a femur bone (2) for the introduction into a bore (3) in the direction of the anatomical axis (4) characterized in that the shaft has projections (5) for a rotationally fixed anchoring; in that the shaft (1) has a terminating collar (6) as a reference abutment for instruments; and in that the shaft (1) has an inwardly disposed parallel guide (7) for a projecting guide part (8) of a coupling piece (10), with the parallel guide (7) being rotationally fixedly arranged in the direction of a mechanical axis (9) which is pivoted towards the medial by a guide angle a with respect to the shaft axis (11) coinciding with the anatomical axis (4).

2. Modular instrument system in accordance with claim 1 characterized in that the shaft has at its front surface (12) which adjoins the collar (6) a positioning receiver or seat (13) for a drive-in device (14) with an enlarged indication of the angle of rotation (15) of the shaft (1) with respect to a frontal or sagittal plane.

3. Modular instrument system in accordance with claim 1 characterized in that the coupling piece (10) is formed as an angled piece (16) of which the first limb (17) is arranged perpendicular to the projecting guide part (8) and of which the second limb (18) is arranged anteriorly and parallel to the guide part (8), with the parallel distance being chosen to be so large that the second limb (18) can have no contact with intervening femur bone parts.

4. Modular instrument system in accordance with claim 3 characterized in that the second limb is provided with at least one guide slot (19) which extends parallel to the guide part (8) in order to enable an auxiliary guiding against rotation with the guide slot (19) for a support element (20) which can be mounted on the femur bone.

5. Modular instrument system in accordance with claim 1 characterized in that a resection block (21, 24) can be mounted on the coupling piece (10) in a predetermined orientation position with respect to the coupling piece (10) in order to enable resections which are compulsorily in a predetermined orientation with respect to the mechanical axis (9).

6. Modular instrument system in accordance with claim 1 characterized in that manipulation condyles (23) can be fastened to the end face of the first limb (17) in a predetermined orientation in order to make the location of the final positions of a joint articulation checkable with respect to a manipulation platform (38) for the tibia (25).

7. Modular instrument system in accordance with claim 6 characterized in that, on the reverse side of the first limb (17), spacers of different thicknesses can be inserted to lie in contact at the manipulation condyles (23) and at the collar (6) as reference abutments (30) in order to determine the ideal distance in the guide direction of the mechanical axis (9) for the later artificial condyles.

8. Modular instrument system in accordance with claim 6 characterized in that artificial condyles of different sizes and manipulation condyles (23) of different sizes corresponding to them are provided.

9. Modular instrument system in accordance with claim 1 characterized in that a plurality of shafts are present which differ in their lengths and in the size of the guide angle a between the shaft axis (11) and the guide direction or, respectively, between the anatomical axis (4) and the mechanical axis (9).

10. Modular instrument system in accordance with claim 9 characterized in that the shafts are made in two parts with a lock (27) in order to combine a plurality of shaft lengths and guides with different guide angles a.

* * * * *